United States Patent [19]

Rohrer et al.

[11] Patent Number: 4,956,155
[45] Date of Patent: Sep. 11, 1990

[54] METHOD AND APPARATUS FOR STERILIZING CONTACT LENSES

[75] Inventors: Michael D. Rohrer, Norman; Ronald A. Bulard, Oklahoma City, both of Okla.

[73] Assignee: The Board of Regents of the University of OK, Norman, Okla.

[21] Appl. No.: 330,602

[22] Filed: Mar. 29, 1989

Related U.S. Application Data

[60] Continuation of Ser. No. 20,375, Mar. 2, 1987, which is a division of Ser. No. 730,381, May 3, 1983, Pat. No. 4,671,935, which is a continuation-in-part of Ser. No. 553,788, Nov. 21, 1983, Pat. No. 4,599,216.

[51] Int. Cl.$^5$ ............................................. A61L 2/26
[52] U.S. Cl. ........................................ 422/297; 206/5.1; 219/10.55 E; 250/455.1; 422/21; 422/292; 422/300; 422/310
[58] Field of Search ............... 422/21, 292, 297, 300, 422/310; 250/455.1; 219/10.55 E; 206/5.1

[56] References Cited

U.S. PATENT DOCUMENTS

| | | | |
|---|---|---|---|
| 3,494,722 | 2/1970 | Gray | 422/21 |
| 3,676,058 | 7/1972 | Gray | 422/22 X |
| 4,011,941 | 3/1977 | Parsons | 206/5.1 |

Primary Examiner—Robert J. Warden
Assistant Examiner—Jill Johnston
Attorney, Agent, or Firm—Dunlap, Codding, Peterson & Lee

[57] ABSTRACT

Apparatus for sterilizing contact lenses wherein the lenses are moved in a circular orbit within a microwave oven through variations of energy levels in the microwave field in the oven, with the orbit of movement being spaced from the floor of the oven.

2 Claims, 1 Drawing Sheet

METHOD AND APPARATUS FOR STERILIZING CONTACT LENSES

This is a continuation of application Ser. No. 07/020,375 filed on Mar. 2, 1987 entitled Apparatus for Sterilizing Contact Lenses. Ser. No. 07/020,375 is divisional of application Ser. No. 06/730,381, filed 5/3/83 now U.S. Pat. No. 4,671,935, entitled Method and Apparatus for Sterilizing Contact Lenses. Ser. No. 06/730,381 is a continuation-in-part of application Ser. No. 06/553,788, filed 11/21/83 now U.S. Pat. No. 4,599,216, entitled Apparatus for Exposure to Microwaves.

BACKGROUND OF THE INVENTION

Approximately ten to fifteen million people in the United States use daily-wear soft contact lenses The major problem with the wearing of these lenses is the possibility of corneal infection. This is primarily the result of two factors, the inability of the patient to sterilize the lenses without damaging them, and the fact that a scratch on the cornea, which is extremely susceptible to becoming infected, will not hurt when covered by the comfortable soft contact lens.

Of the three main types of contact lenses, daily-wear hard lenses, daily-wear soft lenses and extended-wear soft lenses, only the daily-wear soft lenses present a major problem of infection. It is the wearers of these lenses that have a problem due to the lack of an adequate means of home sterilization. The present methods of disinfection of soft lenses have inherent problems. The chemical method results in almost all patients becoming allergic to the preservatives in the solutions and, therefore, unable to use the disinfecting method. The heat method requires a long term, often overnight, heating of the lenses in a solution. This requirement for a very demanding disinfection procedure results in poor patient compliance. Heat disinfection also causes damage to the lenses.

Another problem involving lens sterilization is that of sterilizing bandage lenses. A bandage lens is a high water content hydrophilic extended-wear soft contact lens. It is used to protect the cornea in a variety of situations such as protection following corneal surgery, and in various disease processes that prevent normal healing of the corneal epithelium, including poorly healing epithelial defects, corneal injuries and ulcerations.

DESCRIPTION OF THE PREFERRED EMBODIMENT

Figure 1:
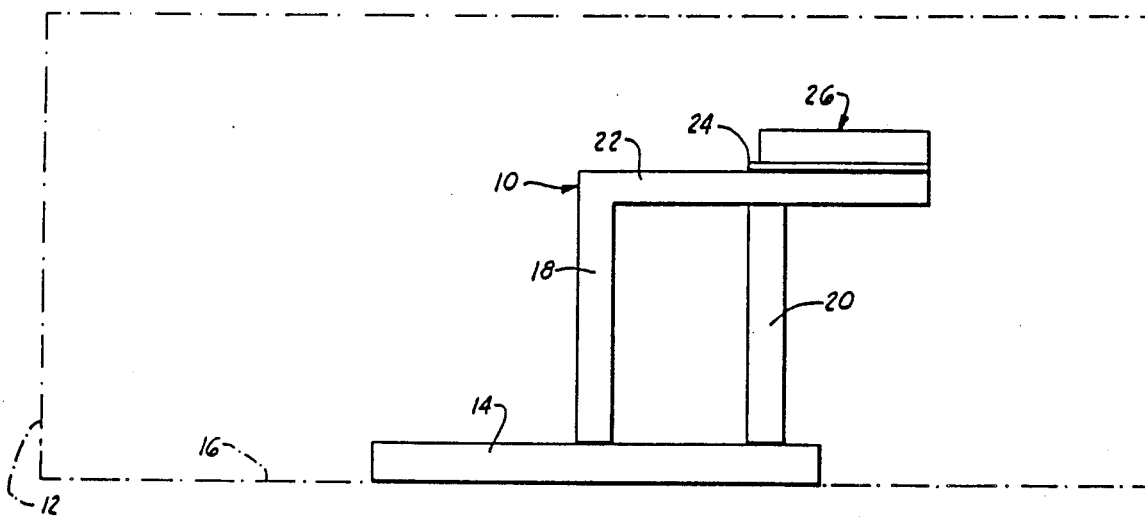
FIG. 1 is a schematic side view of an apparatus constructed in accordance with this invention positioned within a microwave oven which is illustrated in dashed lines.

Referring to the drawings in detail, and particularly FIG. 1, reference character 10 generally designates an apparatus for sterilizing contact lenses in accordance with this invention, positioned within a microwave oven 12 which is shown in dashed lines. The apparatus 10 comprises a turntable 14 positioned on the floor 16 of the microwave oven. The turntable 14 may be of any suitable type, such as a spring driven turntable sold by Nordic Ware of Minneapolis, Minn., under the trademark Micro-Go-Round. An upright portion of the support comprising a pair of posts 18 and 20 are suitably secured to the top of the turntable 14 and extend upwardly to a generally central location within the microwave oven 12. A transverse portion 22 of the support is secured to the upper ends of the posts 18 and 20 to extend transversely from the vertical axis of the turntable 14 in a generally horizontal plane. The transverse portion 22 is formed of a material which is transparent to microwaves, as well known in the art. A pair of horizontally spaced guides 24 (only one of which is shown in FIG. 1) are provided on the top of the transverse portion 22 to slidingly receive a rectangular container generally designated by the reference character 26 therebetween, such that the container 26 will be maintained in an upright position and will be moved through the interior of the oven 12 in a circular orbit oriented on a horizontal plane when the turntable 14 is placed in operation. It should also be noted here that the material of construction of the container 26 is such as to be transparent to microwaves and is preferably a plastic material for safe handling.

Figure 2:
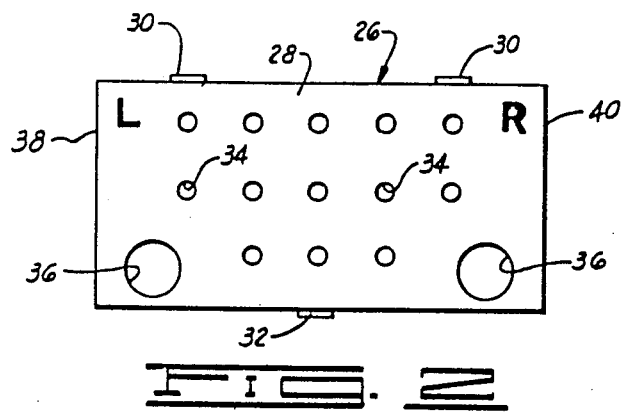
FIG. 2 is a top view of a container for a pair of contact lenses.

As shown in FIG. 2, the top 28 of the container 26 is secured to the body of the container by suitable hinges 30, such that the top 28 may be raised and lowered, and a suitable clasp 32 is provided on the opposite side of the top 28 for securing the top 28 in a closed position. A plurality of apertures 34 are provided through the top 28 for allowing steam to escape from the container 26 when the apparatus is placed in use, as will be described further below. Also, a pair of larger apertures 36 are provided in opposite corners of the top 28 which permit the introduction of saline into the container 28 as will also be described. Finally, an L is preferably placed near one end 38 of the top 28 and an R is preferably placed adjacent the opposite end 40 of the top 28 to indicate to the user where his respective left and right lenses should be placed in the container.

Figure 3:
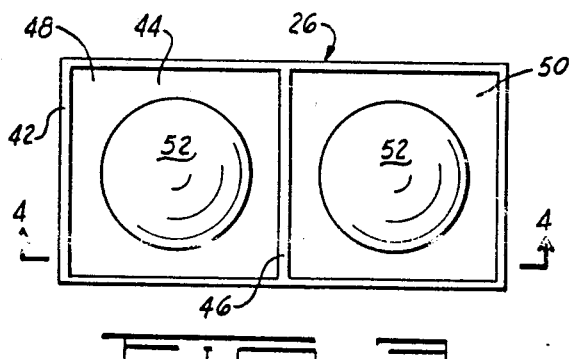
FIG. 3 is a plan view of the container with the top removed.
Figure 4:
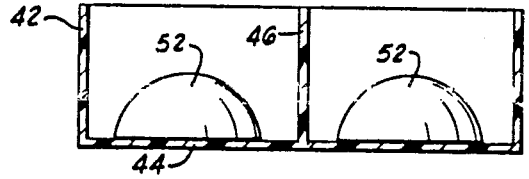
FIG. 4 is a sectional view taken along lines 4—4 of FIG. 3.

As shown in FIGS. 3 and 4, the sides 42 and bottom 44 of the container 26 are preferably solid, and a divider wall 46 extends transversely across the container 26 to divide the container in to left and right sections 48 and 50. A convex protrusion 52 is located or formed on the bottom of the container in each of the left and right sections. Each protrusion 52 is made of a material transparent to microwaves and is of a size to receive a contact lens thereon, such that the contact lens will be maintained in basically its normal configuration during the sterilizing operation to be described below. It may also be noted that the enlarged apertures 36 in the top 28 of the container as illustrated in FIG. 2 are offset vertically from the convex protrusions 52.

OPERATION

Preparatory to sterilization, the lenses are removed from the eye, cleaned in the normal way between the fingers with cleaning solution to remove any protein debris. The cleaned lenses are then placed over the protrusions 52; whereupon the top 28 of the container 26 is closed and the container is placed between the guides 24 on the transverse support member 22 with the apparatus 10 located within the microwave oven 12. The door of the oven is closed, the oven is turned on and the turntable 14 is placed in operation. Thus, the container 26 and the lenses therein will be moved in a circular orbit on a horizontal plane within the oven 12, well above the bottom 16, whereby the lenses will be repetitively subjected to variations of energy levels (hot and cold spots) in the microwave field until the lenses are sterilized.

During operation of the apparatus 10, the lenses will dehydrate, but since the lenses are resting on the convex protrusions 52, each lens will not fold over and touch itself. As the lenses dehydrate, the steam generated thereby is free to escape through the apertures 34 in the top 28.

It should also be noted that a radar absorbent material (not shown) is preferably placed within the microwave oven during the irradiation to act as a load so the microwave oven is not being operated "empty" which could severely damage the magnetron, or energy source, since the unabsorbed microwave energy would be reflected back to the magnetron.

Following irradiation, the container 26 is removed and the patient introduces sterile saline through the apertures 36 before touching the lenses. Since the apertures 36 are vertically offset from the protrusions 52, the saline will be directed onto the bottom of the container and gradually envelope the lenses to assure that no shock loads will be imposed on the lenses which may result in damage. After the container 26 has been partially filled with the saline solution above the level of the lenses and the lenses are fully hydrated, the patient opens the top 28, removes the lenses and places them in the eyes.

Aquaflex TM (tetrafilcon A) hydrophilic contact lenses manufactured by UCO Optics Inc. of Rochester, N.Y., have been sterilized by use of the present invention. Organisms that have been studied to this date for sterilization of the hydrophilic lenses and the time required for sterilization are as follows:

| Organism | Type | Time to Kill |
| --- | --- | --- |
| *Escherecia coli* | Gram negative bacterium | 2–4 minutes |
| *Staphyloccus aureus* | Gram positive bacterium | 6–8 minutes |
| *Streptococcus pneumoniae* | Gram positive bacterium | 30–45 seconds |
| *Proteus vulgaris* | Gram negative bacterium | 1–2 minutes |
| *Candida albicans* | Gram positive fungus | 2–4 minutes |
| *Aspergillus fumigatus* | Gram positive fungus | 2–4 minutes |
| *Pseudomonas aeuriginosa* | Gram negative bacterium | 2–4 minutes |
| *Bacillus cereus* | Gram positive spore forming bacterium | 4–6 minutes |
| *Serratia marcescens* | Gram negative bacterium | 2–4 minutes |
| Herpesvirus type 1 | DNA virus | 2–4 minutes |
| Parainfluenza virus type 3 | Single stranded RNA virus | 1–2 minutes |
| Rhinovirus | Double stranded RNA virus | 2–4 minutes |
| Adenovirus type 1 | Double stranded DNA virus | 2–4 minutes |

Virus contaminated contact lens studies are shown in the following Table.

TABLE 1

| Virus Contaminated Contact lens | Effects of Microwaves on Virus Time of Exposure (minutes)[a] | | | | | | |
| --- | --- | --- | --- | --- | --- | --- | --- |
| | 0 | 1 | 2 | 4 | 6 | 8 | 10 |
| Adeno 1 | +++[b] | ++ | + | 0 | 0 | 0 | 0 |
| HSV-1 | $1.2 \times 10^{6c}$ | $4.5 \times 10^3$ | $3 \times 10^1$ | 0 | 0 | 0 | 0 |
| PI-3 | $1.5 \times 10^5$ | $2 \times 10^3$ | 0 | 0 | 0 | 0 | 0 |
| Rhinovirus | $4 \times 10^5$ | $3 \times 10^2$ | $1.5 \times 10^1$ | 0 | 0 | 0 | 0 |

[a]Virus contaminated contact lens were exposed to micro-waves for 0 to 10 minutes.
[b]+++ = CPE seen in greater than 50% of the cell culture. ++ = CPE seen in 10 to 50% of the cell culture. + = CPE seen in less than 10% of the cell culture.
[c]Plaque forming units per ml.

Changes may be made in the combination and arrangement of parts or elements or steps and procedures without departing from the spirit and scope of the invention as defined in the following claims.

What is claimed is:

1. An apparatus for sterilizing a contact lens in a microwave oven and rehydrating the contact lens with fluid, said apparatus being insertable into a microwave oven having a floor, comprising:
    a container constructed of a material which is transparent to microwaves having a bottom, a top, and at least one side wall wherein the bottom and the side wall cooperate to form a retaining space capable of retaining fluid;
    means for supporting a contact lens in the retaining space capable of permitting contact between the contact lens and the fluid and capable of preventing any portion of the contact lens from touching another portion of the contact lens;
    means for rehydrating the contact lens with fluid after radiating the contact lens with microwaves; and
    means for moving the container through various locations of microwave energy levels within the oven in spaced relation from the floor of the oven until the lens is sterilized comprising:
    a turntable adapted to rest on the floor of the microwave oven; and
    a support comprising an upright portion extending upwardly from the turntable and a transverse portion which extends transversely from the center of the turntable adapted to support the container in spaced relation from a vertical axis through the turntable.

2. The apparatus of claim 1 wherein the transverse portion of the support is characterized by a portion on which the container rests, and wherein said transverse portion is transparent to microwaves.

* * * * *